United States Patent [19]

Hung et al.

[11] Patent Number: 4,963,160
[45] Date of Patent: Oct. 16, 1990

[54] REACTIVE UV ABSORBING COMPOSITIONS AND METHOD OF PREPARING LENSES THEREFROM

[75] Inventors: William M. Hung; Kai C. Su, both of Alpharetta, Ga.

[73] Assignee: Ciba-Geigy Corporation, Ardsley, N.Y.

[21] Appl. No.: 323,327

[22] Filed: Mar. 14, 1989

[51] Int. Cl.$^5$ .............................................. D06P 5/00
[52] U.S. Cl. ............................................ 8/507; 8/549; 8/566; 8/648; 8/688; 8/696; 351/159; 351/160 R; 351/160 H; 544/180; 544/190; 544/194; 544/204
[58] Field of Search ............................ 8/507, 566, 648,

[56] References Cited

U.S. PATENT DOCUMENTS

| | | | |
|---|---|---|---|
| 4,303,701 | 12/1981 | Torgersen et al. | 8/507 |
| 4,390,676 | 6/1983 | Loshaek | 526/313 |
| 4,468,229 | 8/1984 | Su | 8/507 |
| 4,528,311 | 7/1985 | Beard et al. | 524/91 |
| 4,553,975 | 11/1985 | Su | 8/507 |
| 4,559,059 | 12/1985 | Su | 8/507 |
| 4,702,574 | 10/1987 | Bawa | 8/507 |
| 4,719,248 | 1/1988 | Bambury et al. | 523/108 |
| 4,891,046 | 1/1990 | Wittmann et al. | 8/507 |
| 4,929,250 | 5/1990 | Hung | 8/507 |

Primary Examiner—A. Lionel Clingman
Attorney, Agent, or Firm—Irving M. Fishman; Edward McC. Roberts

[57] ABSTRACT

An ultraviolet radiation absorbing agent for bonding to an ocular lens, wherein the agent has the formula:

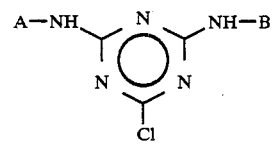

wherein A and B are ultraviolet radiation absorbing components which are either identical to or are dissimilar to each other.

10 Claims, No Drawings

REACTIVE UV ABSORBING COMPOSITIONS AND METHOD OF PREPARING LENSES THEREFROM

BACKGROUND OF THE INVENTION

The present invention relates to reactive ultraviolet radiation absorbing compositions and a method of preparing lenses therefrom. More particularly, the present invention relates to such lenses having two UV absorbing components bonded to a polymeric lens material Ultraviolet radiation is ever present in our environment, and consists of wave lengths between 200–400 nm. Exposure to ultraviolet radiation has been found to be the cause of several ocular pathologies. The damaging effect of ultraviolet radiation on the corneal epithelium has been known for a long time. More recent studies demonstrate the damaging effect of 290 nm radiation on the rabbit corneal epithelium (Cullen, A. P. (1980): *Ultraviolet Induced Lysosome Activity in Corneal Epithelium,* Graefes Arch Clin Exp. Ophthalmol 214:107–118), as well as changes in the stroma and endothelium of primary corneal layers (epithelium, stroma and endothelium) subsequent to exposure to a commercially available UV suntan lamp which emits radiation across the full spectrum from 280 nm (Ringvold, A., et al. (1980): *Changes in the Rabbit Corneal Stroma Caused by UV-Radiation,* Acta Ophthalmol. (Copenh, 63:601–606). Also, ultraviolet radiation damage to the eye is known to be cumulative and obeys the law of reciprocity. These findings reinforce the importance of adequate ocular protection against ultraviolet radiation. Such protection is particularly recommended for people who are prone to UV exposure, patients who have had cataract surgery and patients on photo-sensitizing drugs.

Recently, contact lenses have been developed which absorb ultraviolet radiation. For example, U.S. Pat. No. 4,390,676 discloses an ultraviolet absorbing contact lens formed by copolymerizing a monomer suitable for making lenses and an ultraviolet absorber for absorbing radiation having wavelengths of 340 to 450 nm. A UV absorbing compound, 2-hydroxy-4-methacryloxy-benzophenone, is incorporated into the lens' polymeric material at the molecular level. Also, U.S. Pat. No. 4,528,311 discloses an ultraviolet light absorbing contact lenses made of a polymeric composition comprising copolymers of 2-hydroxy-5-acrylyloxyphenyl-2H-benzotriazole with one or more other monomers copolymerizable therewith.

The above described UV absorbing lenses possess several limitations. For instance, the absorbing agents and the lens material have different properties, and only one absorbing agent is used and appears symmetrically as a thick film on the lens. As a result, the lenses have structural weaknesses and exhibit inconsistent expansion, which in turn results in overly curved or otherwise misshapened lenses. Furthermore, the application of the agent to the lens takes a relatively long time, must be done at high temperature, and requires a high concentration of the expensive agent. Also, the use of a single absorbing agent limits the range of UV wavelengths which the lens may absorb.

There exists, therefore, a need for improved ultraviolet radiation absorbing contact lenses, as well as a method for their production.

There also exists a need for such lenses which have structural integrity, which can be prepared in relatively short time and at relatively low temperatures and which use small amounts of UV absorbing agents.

There exists a further need for such lenses which absorb a broad range of UV wavelengths.

SUMMARY OF THE INVENTION

The present invention relates to ultraviolet absorbing lenses, including contact lenses, which are comprised of a UV absorbing agent incorporated into polymeric lens material. The absorbing agent has the formula:

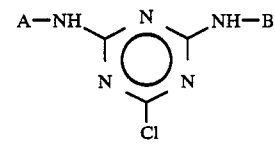

wherein A and B are ultraviolet radiation absorbing components. The agent should be water soluble because the step of incorporating the agent onto the lens material is performed in an aqueous medium. The polymeric lens material can be any of the conventional compositions used in lens construction, such as hydroxyethyl methacrylate (HEMA), which provide the polymer with the required exoskeletal functional groups, such as hydroxyl, amino, amide and mercapto groups, that interact with the absorbing agent.

The UV absorbing components A and B may be similar or different. If A and B absorb radiation of different wavelengths, a lens having the agent with both components will be capable of absorbing radiation having wavelengths of the union of A and B. Also, regardless of whether the A and B components are similar or different, less agent will be needed on the lens.

It has also been found that the absorbing agent of the present invention can be applied to a lens at about room temperature and in a relatively short time by simply dipping or otherwise placing the lens into an aqueous medium having the agent dissolved therein. This enables the agent to be applied to the lens by an optometrist at the point of purchase, rather than at the facility where the lens is made. Therefore, the optometrist does not need to maintain a large inventory of already absorbent lenses.

It is an object of the present invention, therefore, to provide an improved ultraviolet radiation absorbing contact lens.

It is also an object of the present invention to provide such a lens which has structural integrity, which can be prepared quickly and at low temperatures, and which incorporates a relatively small amount of absorbing agent.

It is a further object of the present invention to provide such a lens which can absorb a broad range of ultraviolet wavelengths.

DETAILED DESCRIPTION OF THE INVENTION

While the present invention is applicable to intraocular lenses and lenses used in spectacles, it will be described in connection with contact lenses. The present invention relates to lenses having a UV absorbing agent bonded to its polymeric lens material The absorbing agent is water soluble and has a molecular structure which contains two UV absorbing components thereon which may either be the same or different from each other.

The composition of the polymeric lens material may vary so long as there is present in the monomer mixture a component which will provide the polymer with the required exoskeletal functional groups. Examples of such functional groups include hydroxyl, amino, amide, and mercapto groups. Suitable monomers include hydroxyalkyl esters of polymerizable unsaturated acids, such as acrylic, methacrylic, fumaric and maleic acids. In addition to hydroxyalkyl esters of unsaturated acids, the following monomeric materials may serve as typical examples of co-monomer which can be used in conjunction with monomers providing the required functional groups include alkyl and cycloalkyl acrylates and methacrylates; N-(1, 1-dimethyl-3-oxobutyl) acrylamide; and heterocyclic N-vinyl compounds containing a carbonyl functionality adjacent to the nitrogen in the ring, such as N-vinyl pyrrolidone. A cross-linking agent, such as ethylene glycol dimethacrylate or diethylene glycol bis-allyl carbonate, may be used to provide the polymeric material. A preferred lens material is hydroxyethyl methacrylate (HEMA), as disclosed in U.S. Pat. No. 2,976,576 and U.S. Pat. No. Re. 27,401. An example of a "hard" contact lens material having an acceptable functional group is cellulose acetate butyrate.

The present invention employs a water soluble reactive ultraviolet radiation absorbing agent of the following formula:

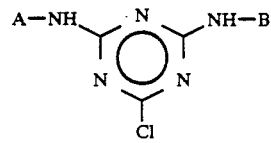

wherein A and B are ultraviolet radiation absorbing components. The ultraviolet radiation absorbing components (A and B) may be identical or different. Examples of suitable components include p-aminobenzoic acid, p-amino salicyclic acid, substituted benzophenone and substituted benzotriazoles. The agent should be water soluble because the process for applying the absorbing agent onto the lens material includes steps carried out in an aqueous medium.

The invention can be illustrated in the following examples:

EXAMPLE I

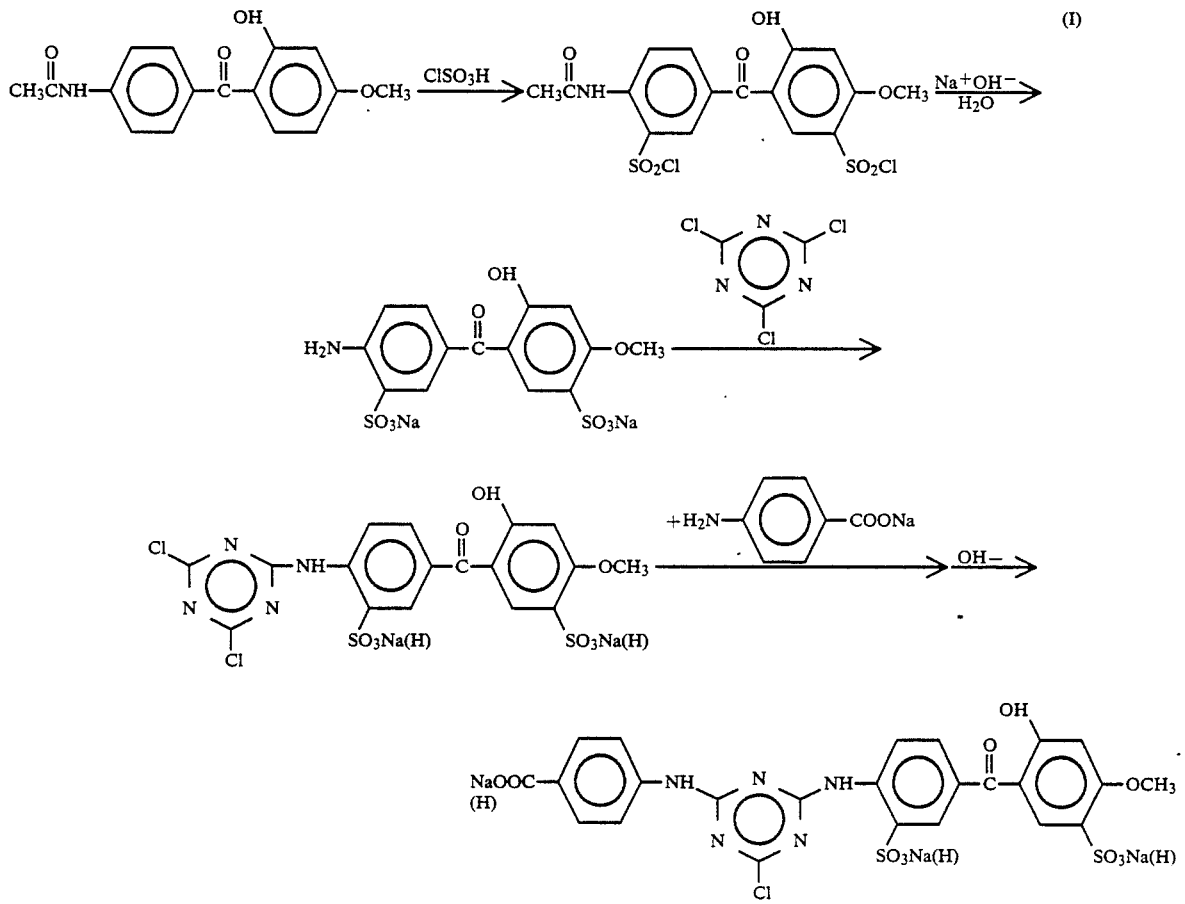

A. 100 ml of chlorosulfonic acid was charged into a 500 ml flask and cooled to 5° C. Then, 20 g of 4'-acetamido-2-hydroxy-4-methoxybenzophenone was added to the flask over a period of 15 minutes. The reaction was maintained at a temperature below 20° C. during the addition. After the addition, the reaction mixture was stirred at room temperature for 16 hours. The reaction mixture was added dropwise into 1.5 liters of ice water and a precipitate was formed. The precipitate was collected and washed two times with 50 ml of ice water, then air dried.

The precipitate was placed in 120 ml of water, and dilute NaOH was slowly added until the solid dissolved. The solution had a pH of 12 and was kept at 90° C. for 30 minutes, then cooled to room temperature.

B. A cyanuric chloride suspension was prepared by dissolving 12 g of cyanuric chloride in 50 ml of warm acetone and quickly dispersed into 150 ml of ice water. At 5° C., the solution from part A was quickly added to the cyanuric chloride suspension. The reaction mixture was stirred at approximately 10° C. for three hours whereby a gel material was formed. Water was added to dilute the gel material until the total volume was 400 ml and the pH was 3.0.

C. A mixture of 100 ml of the gel material solution from part B, 2.5 g of p-aminobenzoic acid which was predissolved in dilute base, 3.0 g of sodium carbonate and 100 ml of water was heated at 90° C. for three hours. The mixture was then cooled to room temperature and the pH was adjusted from 9.2 to 7.0 with 3N.HCl. The solution was then evaporated to dryness and the residue was extracted with hot acetone several times to obtain hydroxy-4-methoxy-5-sulfo)benzoyl]-phenylamino}-s-triazine (compound I) and/or its sodium salts as a yellow solid, which was the ultraviolet radiation absorbing agent.

EXAMPLE II temperature for four hours. The mixture was then quenched dropwise into 1.5 liters of ice water and a precipitate was formed. The precipitate was collected, washed two times with 50 ml of ice water, and air dried to obtain 28.5 g.

28.3 g of the precipitate was suspended in 150 ml of water. 25% NaOH was slowly added to dissolve the precipitate and the pH of the solution was adjusted to 11.5 and was kept at 90° C. for thirty minutes, then cooled to room temperature. The resulting orange solution had a total volume of 300 ml.

B. A cyanuric chloride dispersion was prepared by dissolving 15 g of cyanuric chloride in 70 ml of warm acetone and quickly dispersed into 200 ml of ice water. The beaker which had been holding the cyanuric chloride was rinsed with an additional 30 ml of acetone, which was then added to the dispersion. The dispersion was cooled to 5° C.

The orange solution from part (A) was quickly added into the cyanuric chloride dispersion and the resulting mixture was stirred at between approximately 5° to 10° C. for three hours. The pH of the mixture was 2.7. A small amount of water was added, and the final volume was adjusted to 900 ml.

C. 225 ml of the mixture from (B), 4.2 g of 4-aminosalicyclic acid, sodium salt dihydrate, 3.0 g of $Na_2CO_3$ and 150 ml of water was mixed. The pH was

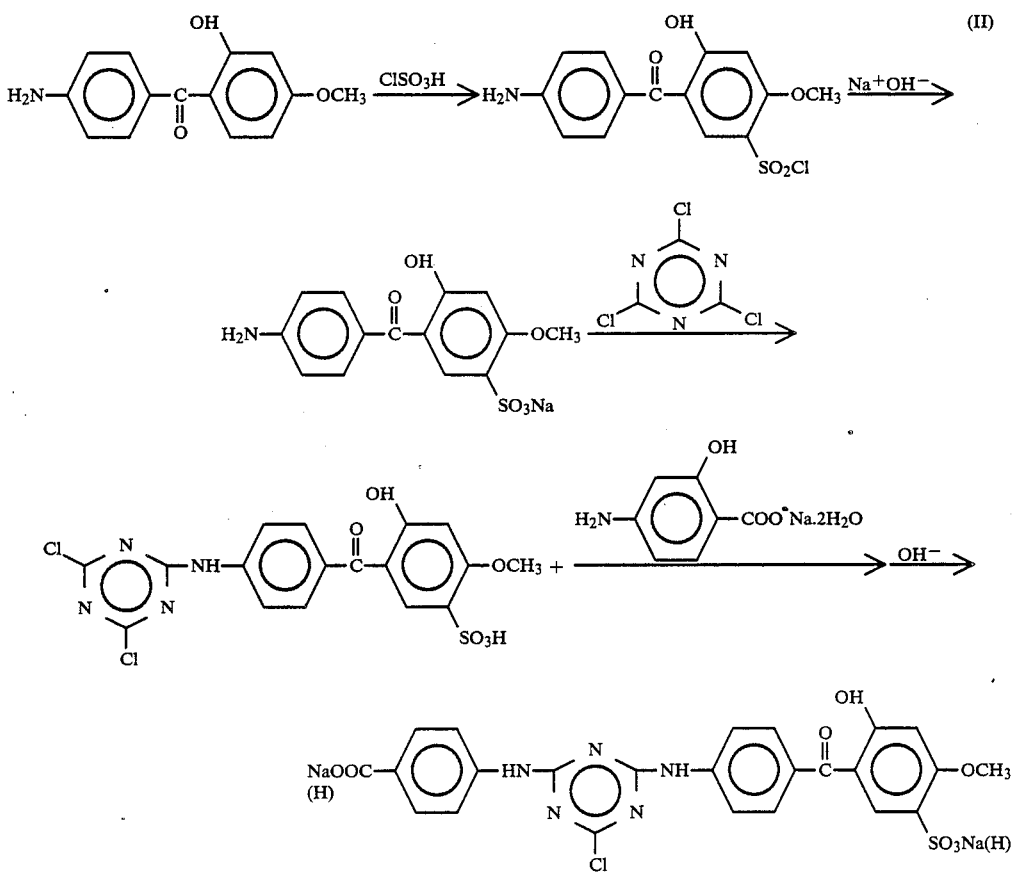

A. 100 ml of chlorosulfonic acid was charged into a flask and cooled at approximately 5° C. in an ice bath. 20 g of 4'-amino-2-hydroxy-4-methoxybenzophenone was slowly added over a period of 20 minutes. The addition was performed at a temperature below 20° C. After addition, the reaction mixture was stirred at room adjusted to 9.5 by adding NaOH, and the reaction mixture was heated at 90° C. for three hours, then cooled to room temperature. The pH was then adjusted to 7.0 with 3N HCl. The mixture was evaporated to dryness.

The residue was extracted with hot acetone several times to get 17.79 g of 2-chloro-4-[(3-hydroxy-4-carboxy)phenylamino]-6-{4-[(2-hydroxy-4-methoxy-5-sulfo)-benzoyl]phenylamino}-s-triazine (Compound II) and its sodium salts, as a yellow solid, which was the UV absorbing agent.

EXAMPLE III

Proceeding in a manner similar to that described in Example I, part C above, except that 4-amino salicyclic acid was substituted for p-aminobenzoic acid, resulted in the formation of 2-chloro-4-[(3-hydroxy-4-carboxy)-phenylamino]-6-{2-sulfo-4-[(2-hydroxy-4-methoxy-5-sulfo)benzoyl]phenylamino}-s-triazine and its sodium salts.

EXAMPLE IV

Proceeding in a manner similar to that described in Example II, part C above, except that p-aminobenzoic acid was substituted for 4-aminosalicyclic acid to obtain 2-chloro-4-[(4-carboxy)phenylamino]-6-{4-[(2-hydroxy-4-methoxy-5-sulfo)benzoyl]phenylamino}-s-triazine and its sodium salts.

A typical process for applying the absorbing agent to the lens is now set forth. A mixture of 2 ml of 0.05 to 5.0% (aq) stock solution of ultraviolet radiation absorbing agent, 2 ml of 5 to 10% (aq) Na$_3$PO$_4$.12H$_2$O, and 0.2 ml of 1 to 10% (aq) solution of tetrabutylammonium bromide was prepared and heated at 50° C. for 60 minutes with agitation. A clear lens comprised of hydroxyethyl methacrylate (HEMA) was then soaked in the mixture until the agent bonded to the lens. The lens was then neutralized with a buffered saline solution (pH=7.0), after which the lens was extracted with 10% glycerine in an extraction bath until there was no UV absorbing agent leaching out. This was determined by a UV spectrophotometer After the extraction process, the lens was boiled in distilled water, and then buffered with saline to remove any remaining glycerine.

It has been found that adding two different UV absorbing components onto the agent can provide a contact lens which will absorb a wide range of wavelengths. For example, the absorbing component Tinuvin ® P (available from Ciba Giegy Corporation), which is a benzotriazole type absorber, blocks UV radiation from about 280 nm to 360 nm very well, but it does not block well at about 250 nm to 275 nm. The 4-aminobenzoic acid type component blocks radiation from 190 nm to 316 nm very well, but little higher. By combining the two components onto a single molecule according to the present invention, the resultant UV absorbing agent, and hence a lens incorporating the agent, will have excellent UV absorption from about 190 nm to 360 nm (the union of the spectra of the two components).

Similarly, when a benzophenone type component (which also blocks UV radiation from about 280 nm to 360 nm) is added to 4-aminobenzoic acid type component in place of the Tinuvin ® P above, the resulting reactive UV absorbing agent will have excellent UV absorption from about 190 nm to 360 nm.

It is also possible to add similar or identical UV absorbing components onto the agent. In such a case, the amount of agent needed to provide an effective radiation absorbing lens will be decreased. The decrease of agent on the lens greatly reduces the structural weaknesses associated with lenses having single-component absorbing agents.

What is claimed is:

1. An ultraviolet radiation absorbing contact lens comprising an effective amount of an ultraviolet radiation absorbing agent bonded to a polymeric lens material, said ultraviolet radiation absorbing agent having the formula:

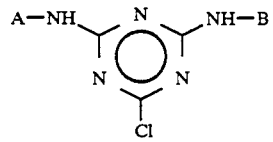

wherein
A is selected from the group consisting of p-aminobenzoic acid, p-aminosalicylic acid, substituted benzophenone and substituted benzotriazoles;
said polymeric lens material has a functional group selected from the group consisting of hydroxyl, amino, amide, and mercapto, and mixtures thereof.

2. The ultraviolet radiation absorbing lens of claim 1 wherein A and B are different components.

3. The ultraviolet radiation absorbing lens of claim 1, wherein A and B are identical components.

4. The ultraviolet radiation absorbing lens of claim 1, wherein said polymeric lens material comprises hydoxyethyl methacrylate.

5. The ultraviolet radiation absorbing lens of claim 1, wherein said polymeric lens material comprises cellulose acetate butyrate.

6. A method of preparing an ultraviolet absorbing contact lens, comprising the steps of contacting a lens made of polymeric lens material with a solution containing an effective amount of an ultraviolet radiation absorbing agent capable of bending with said lens material and removing said lens from said solution after a preselected period of time, said agent having the formula:

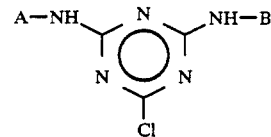

wherein
A is selected from the group consisting of p-aminobenzoic acid, p-aminosalicylic acid, substituted benzophenone and substituted benzotriazoles;
B is selected from the group consisting of p-aminobenzoic acid, p-aminosalicylic acid, substituted benzophenone and substituted benzotriazoles;
said polymeric lens material has a functional group selected from the groups consisting of hydroxyl, amino, amide, and mercapto, and mixtures thereof.

7. The method of claim 6; wherein A and B are different components.

8. The method of claim 6, wherein A and B are identical components.

9. The method of claim 6, wherein said polymeric lens material comprises hydroxyethyl methacrylate.

10. The method of claim 6, wherein said polymeric lens material comprises cellulose acetate butyrate.

* * * * *